United States Patent
Farmer et al.

(10) Patent No.: US 7,854,927 B2
(45) Date of Patent: *Dec. 21, 2010

(54) METHODS AND COMPOSITIONS FOR THE DIETARY MANAGEMENT OF AUTOIMMUNE DISORDERS

(75) Inventors: Sean Farmer, Miami, FL (US); Andrew R. Lefkowitz, Mayfield Heights, OH (US)

(73) Assignee: Ganeden Biotech, Inc., Mayfield Heights, OH (US)

( * ) Notice: Subject to any disclaimer, the term of this patent is extended or adjusted under 35 U.S.C. 154(b) by 277 days.

This patent is subject to a terminal disclaimer.

(21) Appl. No.: 11/127,063

(22) Filed: May 10, 2005

(65) Prior Publication Data

US 2006/0073130 A1    Apr. 6, 2006

Related U.S. Application Data

(60) Provisional application No. 60/569,952, filed on May 11, 2004, provisional application No. 60/571,553, filed on May 13, 2004.

(51) Int. Cl.
*A61K 48/00* (2006.01)
*A01N 63/04* (2006.01)
*C12N 1/20* (2006.01)

(52) U.S. Cl. .................. 424/93.46; 435/252.5; 435/832

(58) Field of Classification Search .................. None
See application file for complete search history.

(56) References Cited

U.S. PATENT DOCUMENTS

| | | | |
|---|---|---|---|
| 6,645,506 B1 * | 11/2003 | Farmer | 424/260.1 |
| 6,849,256 B1 | 2/2005 | Farmer | 424/93.46 |
| 2002/0150594 A1 | 10/2002 | Goldman et al. | 424/234.1 |
| 2003/0045688 A1 | 3/2003 | Chu et al. | 530/351 |
| 2003/0068320 A1 * | 4/2003 | Dingivan | 424/144.1 |
| 2003/0124104 A1 | 7/2003 | Farmer | 424/93.46 |
| 2005/0100535 A1 | 5/2005 | Farmer et al. | 424/93.46 |

FOREIGN PATENT DOCUMENTS

WO    WO 99/49877    10/1999

OTHER PUBLICATIONS

International Search Report for PCT/US05/16469, mailed Dec. 5, 2005.
Mohan et al., "Preliminary observations on effect of *Lactobacillus sporogenes*, on serum lipid levels in hypercholesterolemic patients", *Indian J. Med. Res.*, 92:431-432 (1990).
Sanders et al., "Sporeformers as Human Probiotics: *Bacillus, Sporolactobacillus,* and *Brevibacillus*", *Comprehensive Rev. Food Sci. Food Safety*, 2:101-110 (2003).
DeVecchi et al., "*Lactobacillus Sporogenes or Baccillus Coagulans*: Misidentification or Mislabelling?", *Int. J. Probiotics and Probiotics*, 1(1):3-10 (2006).
Baker et al., "Growth Requirements of 94 Strains of *Thermophilic Bacilli*", *Canadian J. Microbiol.*, 6:557-563 (1960).
*Bergey's Manual of Systematic Bacteriology*, vol. 2, Sneath et al., eds., Williams & Wilkens, Baltimore, MD, p. 1117 (1986).
Nakamura et al., "Taxonomic Study of *Bacillus coagulans* Hammer 1915 with a Proposal for *Bacillus smithii* sp. nov.", *Inter'l J. Systematic Bacteriol.*, 38(1): 63-73 (1988).

* cited by examiner

*Primary Examiner*—Deborah K. Ware
(74) *Attorney, Agent, or Firm*—Mintz Levin Cohn Ferris Glovsky and Popeo, P.C.; Ivor R. Elrifi, Esq.; Ingrid A. Beattie

(57) ABSTRACT

The present invention describes the use of lactic acid bacteria, particularly lactic acid producing members of the genus *Bacillus*, in treating digestive-related immune disorders by downregulating of cytokines and by inhibiting pathogenic or deleterious microorganisms in the gastrointestinal tract. Specific formulations of *Bacillus coagulans* for various immune disorders are elaborated.

27 Claims, No Drawings

METHODS AND COMPOSITIONS FOR THE DIETARY MANAGEMENT OF AUTOIMMUNE DISORDERS

RELATED APPLICATIONS

This application claims priority to U.S. Provisional Application Ser. No. 60/569,952, filed May 11, 2004 (pending) and U.S. Provisional Application Ser. No. 60/571,553, filed May 13, 2004, (pending), the disclosures of which are hereby incorporated by reference herein in their entireties.

BACKGROUND OF THE INVENTION

The invention relates to the treatment of autoimmune disorders.

Gastrointestinal microflora play a number of vital roles in maintaining gastrointestinal tract function and overall physiological health. Perturbations in gastrointestinal function are associated with the onset and progression of immune system disorders, including autoimmune disorders. Autoimmune disorders develop when the immune system mounts an immune response against normal body tissues. Normally, the immune system is capable of differentiating "self" from "non-self" tissue. Autoimmune disorders occur when the normal control process is disrupted. They may also occur if normal body tissue is altered so that it is no longer recognized as "self." Microorganisms, such as pathogenic bacteria, fungi, and viruses, and other causes (drugs, alcohol, smoking, stress) trigger some of these changes, particularly in people with a genetic predisposition to an autoimmune disorder. Autoimmune disorders result in destruction of one or more types of body tissues, abnormal growth of an organ, or changes in organ function. The disorder may affect only one organ or tissue type or may affect multiple organs and tissues. Organs and tissues commonly affected by autoimmune disorders include blood components such as red blood cells, blood vessels, connective tissues, endocrine glands such as the thyroid or pancreas, muscles, joints, and skin.

Psoriasis is a chronic, genetically-influenced autoimmune disorder, most common in people in their 20s, 30s, and 40s. Psoriasis is rare under age 3. In the United States, two or three out of every 100 people suffer from psoriasis. Current topical psoriasis treatments use emollients, keratolytic agents, coal tar, anthralin, corticosteroids, and calpotriene. These approaches have variable efficacy, fail to prevent frequent relapses, and are often associated with adverse side effects. Current systemic treatments are usually reserved for patients with physically, socially, or economically disabling psoriasis that has not responded to topical treatment, and often include phototherapy and/or antifungal drugs, the latter of which can only be used for short periods of time due to toxicity and adverse side effects. Accordingly, there is a need for an effective systemic psoriasis treatment that avoids the disadvantages associated with current topical and systemic treatments.

SUMMARY OF THE INVENTION

The invention provides a method of reducing a symptom of psoriasis by identifying a patient suffering from or at risk of developing psoriasis and administering to the patient a composition that includes *Bacillus coagulans* bacteria. The composition is ingested by a human subject that has one or more symptoms of a dermatological disorder such as psoriasis. Bacterial species include *Bacillus coagulans*, e.g., *Bacillus coagulans* hammer, preferably *Bacillus coagulans* hammer strain Accession No. ATCC 31284, or one or more strains derived from *Bacillus coagulans* hammer strain Accession No. ATCC 31284 (e.g., ATCC Numbers: GBI-20, ATCC Designation Number PTA-6085; GBI-30, ATCC Designation Number PTA-6086; and GBI-40, ATCC Designation Number PTA-6087; see U.S. Pat. No. 6,849,256 to Farmer). Symptoms of psoriasis include scaling, blistering, skin lesions, itchiness, and pain (e.g., joint pain). In embodiments of the invention, the composition also includes a non-microbially derived antifungal agent (e.g., a member of the azole or pyrrole class of antifungal compounds such as clotrimazole, fluconazole, itraconazole, ketoconazole, miconazole, nystatin, terbinafine, terconazole, or tioconazole), an immunosuppressive agent (e.g., methotrexate, tacrolimus, cyclosporine, hydroxyurea, mycophenolate mofetil, sulfasalazine, or 6-thioguanine), a retinoid, or an antibiotic agent (e.g., gentamicin, vancomycin, oxacillin, tetracycline, nitroflurantoin, chloramphenicol, clindamycin, trimethoprim sulfamethoxasole, cefaclor, cefadroxil, cefixime, cefprozil, ceftriaxone, cefuroxime, cephalexin, loracarbef, ampicillin, amoxicillin clavulanate, bacampicillin, cloxicillin, penicillin VK, ciprofloxacin, grepafloxacin, levofloxacin, lomefloxacin, norfloxacin, ofloxacin, sparfloxacin, trovafloxacin, azithromycin, or rythromycin). Administration to the patient includes delivery of the composition(s) via the gastrointestinal tract. The gastrointestinal tract is the system of organs in a mammal including the mouth (buccal cavity), pharynx, esophagus and cardia, stomach(s), and intestines. The bacteria are administered at a dose that reduces a level of TNF-α in the patient.

Following oral administration, colonization of the gastrointestinal tract with *Bacillus coagulans* bacteria occurs between 24-48 hours. Continued colonization is improved by the repeated administration of *Bacillus coagulans*, such as daily administration. For example, a *Bacillus coagulans* bacteria-containing composition is administered (e.g., taken orally) about once every day for about 2, 3, 4, 5, 6, 7, 10, 15, 20, 25, 30, 45, 60, 75, 90, 100, 125 or more days. In embodiments of the invention the *Bacillus coagulans* bacteria are provided at a concentration of from about $1 \times 10^8$ to about $1 \times 10^{10}$ viable bacteria, e.g., at a concentration of from about $1 \times 10^9$ to about $2 \times 10^9$ viable bacteria. The *Bacillus coagulans* bacteria are provided in the form of spores and/or vegetative cells.

The invention also provides a method for the treatment of psoriasis by administering a first dose of a composition containing *Bacillus coagulans* bacteria at a first point in time, and administering a second dose of the composition at a second, subsequent point in time. The bacteria are, for example, *Bacillus coagulans* hammer or bacteria derived from *Bacillus coagulans* hammer strain Accession No. ATCC 31284; available to the public via the ATCC. The treatment includes treating a symptom of psoriasis (e.g., scaling, blistering, skin lesions, itchiness, and joint pain). *Bacillus coagulans* bacteria are provided at a concentration of from about $1 \times 10^8$ to about $1 \times 10^{10}$ viable bacteria, e.g., at a concentration of from about $1 \times 10^9$ to about $2 \times 10^9$ viable bacteria. The *Bacillus coagulans* bacteria are provided in the form of spores or vegetative cells. The composition includes a non-microbially derived antifungal agent, such as an azole, an organic five-membered ring compound containing one or more atoms in the ring. Exemplary azoles include clotrimazole, fluconazole, itraconazole, ketoconazole, miconazole, nystatin, terbinafine, terconazole, or tioconazole. The invention optionally includes administration of an immunosuppressive agent, such as methotrexate, cyclosporine, hydroxyurea, mycophenolate mofetil, sulfasalazine, or 6-thioguanine, or an antibiotic agent, such as gentamicin, vancomycin, oxacillin, tetracycline, nitroflurantoin, chloramphenicol, clindamycin, trimethoprim sulfamethoxasole, cefaclor, cefadroxil, cefixime, cefprozil, ceftriaxone, cefuroxime, cephalexin, loracarbef, ampicillin, amoxicillin clavulanate, bacampicillin, cloxicillin, penicillin VK, ciprofloxacin, grepafloxacin, levofloxacin, lomefloxacin, norfloxacin, ofloxacin, sparfloxacin, trovafloxacin, azithromycin, and rythromycin. The bacteria, antifungal compound(s), and immunosuppressive compound(s) are administered concurrently or sequentially.

The invention also provides a method of reducing a symptom of an autoimmune disorder by identifying a patient suffering from or at risk of developing an autoimmune disorder, and administering to the patient a composition including *Bacillus coagulans* bacteria. The autoimmune disorder is psoriasis, Crohn's Disease, colitis, lupus, arthritis, or any other disorder that is characterized by a pathological increase in activation of immune cells (e.g., T cells) associated with a pathogenic agent (such as a bacteria, fungus or virus).

The invention further provides a method for decreasing a symptom of an autoimmune disorder in a mammal affected thereby, by administering to a mammal a composition that includes *Bacillus coagulans* bacteria. A symptom (e.g., scaling, blistering, skin lesions, itchiness, and/or pain) of the autoimmune disorder is decreased following the administration, compared to the severity of the symptom prior to the administration.

The invention also provides a method for decreasing serum TNF-α or other cytokine levels in a mammal that has been diagnosed with an elevated level of TNF-α, or one or more other cytokines. Normal human serum levels of TNFα range from undetectable to about 40 pg/ml of serum, with average values in the range of 3-10 pg/ml. TNF-α is preferably detected by, e.g., ELISA or other quantitative detection means. (Human TNF-α ELISA kit, Abazyme, Needham, Mass., or Millenia Diagnostic Product, Los Angeles, Calif.).

Serum cytokine levels (such as TNF-α levels) are decreased following the administration of *Bacillus coagulans*, when compared to serum cytokine (such as TNF-α) levels in the mammal prior to the administration. Elevated human serum levels (e.g., greater than about 40, 50, 60, 75, 85, 100, 125, 150, 200, 250, 300, or more pg/ml) prior to administration are associated with autoimmune disorders, and are reduced following a course of administration of *Bacillus coagulans*. A reduction in TNF-α levels confers a clinical benefit to the treated subject, e.g., a reduction in a symptom of an autoimmune disorder. The decrease is any measurable decrease, such as a decrease greater than about 1%, 5%, 10%, 15%, 25%, 50%, 60%, 75%, 85%, 90%, 95%, 99%, 99.9%, 99.99% or greater. The *Bacillus coagulans* bacteria are provided at a concentration of from about $1\times10^8$ to about $1\times10^{10}$ viable bacteria, such as $5\times10^8$, $8\times10^8$, $1\times10^9$, or $5\times10^9$ viable bacteria.

The invention further provides a composition that includes a *Bacillus coagulans* bacterium, and an immunosuppressive agent. The composition is in the form of a capsule, tablet, powder, or liquid. The *Bacillus coagulans* bacteria can be *Bacillus coagulans* hammer or derived from *Bacillus coagulans* hammer, e.g., *Bacillus coagulans* hammer strain Accession No. ATCC 31284.

The invention also provides a system containing medical food for the management of psoriasis or other disorder that includes *Bacillus coagulans* bacteria, where the medical food is formulated to provide at least about $1\times10^6$ viable *Bacillus coagulans* bacteria in the gastrointestinal tract of a mammal per day, based on a serving size of about 1 gram to about 2 grams of the medical food taken up to about twice a day, and instructions for use thereof. In embodiments of the invention, the medical food optionally includes a non-microbially derived anti-fungal agent, an immunosuppressive agent, or a non-microbially derived anti-fungal agent and an immunosuppressive agent.

Other features and advantages of the invention will be apparent from the following detailed description and from the claims.

DETAILED DESCRIPTION

The mammalian gastrointestinal tract is a complex ecosystem host to a diverse and highly evolved microbial community composed of hundreds of different microbial species. A perturbation of the interactions that occur between this complex microbial community and the mammal can lead to diseases such as illnesses associated with deficient or compromised microflora (e.g., gastrointestinal tract infections, inflammatory bowel diseases (such as Crohn's disease and ulcerative colitis), irritable bowel syndrome, antibiotic-induced diarrhea, constipation, food allergies, cardiovascular disease, psoriasis, and certain cancers. "Functional food," e.g., those that contain beneficial bacteria such as *Bacillus coagulans* are useful as therapies to prevent autoimmune diseases and other diseases characterized by an increase in TNF-α compared to normal, control levels.

Lactic acid bacteria (LAB) display numerous health benefits beyond providing general digestive value. They cooperatively maintain a physiological balance between the gastrointestinal tract and immune system. When this balance is disrupted, disease and inflammation often result. Deleterious bacteria are competitively inhibited by the mucosal adherence or transient colonization of beneficial microflora such as *Bacillus coagulans*. A healthy gastrointestinal tract with adequate mucus production and appropriate bacterial colonization prevents or inhibits the growth of pathogenic or opportunistic microorganisms, modulates disease processes, and prevents widespread inflammatory disorders.

*Bacillus coagulans* is an L+ lactic acid-producing bacterium that has been shown to be highly effective in the colonization of the various mucosal surfaces of the gastrointestinal tract. Unlike strictly vegetative species of lactic acid bacteria (e.g., *Lactobacillus, Bifidobacterium*, and other bacteria) that are used in therapeutic applications, *Bacillus coagulans* survives intact after exposure to extremely low pH of stomach and bile acids. This is accomplished due to the extremophile nature of the vegetative form of this organism (thermo-tolerant, acidophilic, baro-tolerant, and halo-tolerant), and that it forms endospores. In addition, *Bacillus coagulans* is highly competitive, which is an important feature for the high-density colonization that is required to promote physiological changes in the small and large bowel. Further, *Bacillus coagulans* has been shown in Minimum Inhibitory Concentration (MIC) dilution (in vitro) studies to inhibit many enteric bacterial pathogens (*Escherichia, Proteus, Clostridium, Campylobacter, Shigella, Salmonella, Enterococcus, Staphylococcus, Streptococcus*, and others), which require a higher than neutral pH in order to proliferate. MIC studies have also been performed that indicate high inhibitory activity on various mycotic pathogens challenged with *Bacillus coagulans*.

The methods and compositions of the present invention are useful in the treatment of autoimmune diseases. Autoimmune diseases can affect almost any organ or tissue of the body, and are thus amenable to classification by the affected tissue(s). It is recognized that an autoimmune disease or disorder can impact one or more tissues. Autoimmune disorders that affect the blood or vasculature including autoimmune hemolytic anemia, pernicious anemia, polyarteritis nodosa, systemic lupus erythematosus, and Wegener's granulomatosis. Autoimmune disorders of the gastrointestinal system include autoimmune hepatitis, Behçet's disease, Crohn's disease, primary biliary cirrhosis, scleroderma, ulcerative colitis, and Irritable Bowel Syndrome (IBS). Autoimmune disorders that affect the ocular system include Sjögren's syndrome, type 1 diabetes mellitus, and uveitis. Autoimmune disorders that affect the endocrine system include Graves' disease, and thyroiditis. Autoimmune disorders that affect the cardiovascular system include myocarditis, rheumatic fever, scleroderma, and systemic lupus erythematosus. Autoimmune disorders that affect connective tissue include ankylosing spondylitis, rheumatoid and reactive arthritis, and systemic lupus erythematosus. An autoimmune disorder that affects the kidneys is glomerulonephritis. An autoimmune disorder that affects the lungs is glomerulonephritis is sarcoidosis. Autoimmune disorders that affect the musculoskeletal system include dermatomyositis, myasthenia gravis, polymyositis, and fibromialgia. Autoimmune disorders that affect the neurological system include Guillain-Barré syndrome, and multiple sclerosis. Autoimmune disorders that affect the skin include alopecia areata, pemphigus (also termed pemphigoids), psoriasis, and vitiligo.

Symptoms of autoimmune disease include fatigue, dizziness, malaise, fever, and decreased platelet and/or eosinophil counts. Further, certain autoimmune diseases are characterized by destruction of a type of tissue (e.g., destruction of islet cells of the pancreas in diabetes) or the increase in organ size (e.g., thyroid enlargement in Graves Disease). For treatment or prevention of such diseases or conditions and reduction of symptoms associated with these conditions, compositions that contain *Bacillus coagulans* bacteria are administered according to the methods described herein.

TNF-α is a naturally occurring cytokine, which is produced by activated immune cells. However, excessive activation of immune effector cells and overproduction of TNF-α can cause severe inflammation and tissue damage. TNF-α plays a major role in a number of disease states, e.g., psoriasis, Crohn's disease, rheumatoid arthritis, ulcerative colitis, and ankylosing spondylitis. Reducing the level of TNF-α in patients suffering from or at risk of developing autoimmune disease or inflammatory disease states alleviates symptoms of the disease and prevents or slows disease progression.

Reducing TNF-α by administering *Bacillus coagulans* confers a clinical benefit (e.g., reduced inflammation) with little or none of the side effects associated with other, non-microbial TNF-α inhibitors (e.g., infliximab, etanercept, and adalimumab). Administration of *Bacillus coagulans* confers a clinical benefit to subjects identified as suffering from or at risk of developing the following exemplary autoimmune disorders.

Psoriasis

Psoriasis is a skin disease that is characterized in part by abnormal proliferation and differentiation of keratinocytes, T-cell and endothelial cell activation, local vascular changes, and neutrophil accumulation as well as other immunological processes, e.g., altered levels of cytokines. Results of cyclosporine and fluconazole treatments also demonstrate that bacterial and mycotic agents play a significant role in psoriasis.

Psoriasis generally results from a genetic defect in combination with external triggers that affect the features of the disease. The cellular immune system plays a dominant role in exacerbation of psoriasis. Microorganisms such as β-hemolytic *streptococci*, *Staphylococcus aureus* and *Candida albicans* are external triggers that release factors which serve as superantigens, and stimulate the T cells to initiate psoriasis, which often resulting in a "pathogenic circle" of repeated incidences of the disease. The source of the microorganisms may be in the skin itself or in distal locations, such as *Streptococcus* in the throat or *Candida albicans* in the gut. From these locations, the microorganisms cause the release of superantigens that travel through the host's vascular system to reach the skin and initiate the psoriatic process.

There are many different forms of psoriasis, including plaque psoriasis (vulgaris psoriasis), guttate psoriasis, pustular psoriasis, erythrodermic psoriasis, nail psoriasis, scalp psoriasis, inverse psoriasis, and psoriatic arthritis. Symptoms of psoriasis vary among the forms of psoriasis, and between affected individuals. As used herein, a "symptom" of psoriasis includes any observable, measurable or detectable sign or indication of any form of psoriasis or a psoriasis-related condition. A patient suffering from psoriasis has one or more symptoms of psoriasis. Psoriasis symptoms include scaling, blistering, skin lesions, itchiness, and joint pain. Other symptoms of psoriasis are known to those of ordinary skill in the art. Psoriasis is diagnosed by the observation or detection of one or more symptoms of psoriasis. Generally, a patient suffering from or at risk of developing psoriasis has one or more symptoms of psoriasis, or a family member having psoriasis or a symptom of psoriasis.

Indications of treatment of psoriasis include any detectable change (e.g., a decrease or disappearance) in a symptom of psoriasis, as measured by size, severity, duration, or the presence or absence of relapses of affected skin. A preferred method of determining the efficacy of a treatment is the measurement of the change in the total psoriatic lesion area following *Bacillus coagulans* treatment, as compared to the in total psoriatic lesion area prior to treatment. Also, a measurable decrease in the amount of serum TNF-α in a patient undergoing psoriasis treatment indicates the efficacy of the treatment. Further, the efficacy of treatment can be determined by the decrease in pathogenic microorganisms present in the gastrointestinal tract of the patient undergoing treatment, such as by measuring the presence of these microorganisms in stool measurement in stool or other biological materials.

Inflammatory Bowel Disease

Human inflammatory bowel disease (IBD) is a group of intestinal inflammatory diseases that can be subdivided in ulcerative colitis (UC) and Crohn's disease (CD) based on typical clinical manifestations. The symptoms of both are extremely unpleasant and impact all aspects of quality of life. They include diarrhea, abdominal pain, rectal bleeding, fever, nausea, weight loss, lethargy and loss of appetite. If left untreated, malnutrition, dehydration and anemia follow, which, in extreme cases, lead to death. Although UC and CD show a considerable degree of similarity in etiology and epidemiology, they are entirely different in pathology. UC is restricted to the colon. CD, however, has been observed throughout the entire intestinal tract, from the mouth to the rectum. Inflammation is restricted to the mucosa in UC, whereas in CD the inflammation can be transmural, i.e., penetrating the bowel wall. This often leads to the development of perianal fistulae. An imbalance in T-helper (Th) subsets of T cells, so called Th1 and Th2, differentiates CD from UC on an immunological basis. In UC, an over-expression of Th2 type cytokines (IL-4, IL-5) has been demonstrated, whereas in CD, Th1 type cytokines (IL-12, IFN-γ) predominate.

CD and UC involve an interaction between genetic and environmental factors, such as bacterial agents. Abnormal immune responses, driven by the intestinal microflora, occur in IBD. Most experimental models for IBD cannot be established in germ-free animals. In one art-recognized experimental model, IL-10−/− mice show that the appearance of mucosal adherent colonic bacteria is causative of the development and maintenance of the inflammation.

Breach of tolerance towards normal intestinal microflora may thus be the driving force behind IBD. The absence of tolerance to the indigenous microflora also appears in trinitrobenzene sulphonic acid (TNBS)-induced colitis. The administration of IL-10, a central mediator in down-regulation of immune reactions, restores healthy status by reestablishing tolerance. This treatment does not, however, affect immune reactivity towards heterologous bacterial antigen. Staphylococcal enterotoxin B can abrogate self-tolerance at the intestinal epithelium. IL-10 can counteract this by preventing the activation of T cells that contribute to epithelial cell damage. T-cell clones stimulated by indigenous aerobic flora and bifidobacteria were also identified in patients with IBD.

Higher bacterial load has been reported in the mucus of IBD patients. Although a number of reports measure no significant differences in the flora composition of UC patients when compared with controls, two recent studies indicate significant decrease of lactobacilli in UC. There are conflicting reports on the composition of the microflora in CD although it is difficult to compare disease stages when assessed in different centers. Bifidobacterium species are found to be decreased in CD. A significant increase in *Escherichia coli* and *Bacteroides fragilis* was detected in the ileum and of *E. coli* and *lactobacilli* in the colon, although *lactobacilli*, together with bifidobacterial scores, have also been found significantly reduced in CD patients.

The development of IBD is in some cases linked to viral or bacterial infection (*Mycobacteria, Shigella, Salmonella, Yersinia, Clostridium difficile, Bacteroides vulgatus*) but to date no etiological agent has been identified for IBD. Recently, however, a DNA sequence has been identified in lamina propria mononuclear cells of which the presence and serum reactivity towards the according peptide highly correlates with CD. This presently unknown sequence is not of human origin and shows homology with bacterial tetR/acrR transcription regulators.

Systemnic Lupus Erythematosus (SLE)

An inflammation of the connective tissues, SLE impacts one or more organs or tissues in a subject. It is up to nine times more common in women than men. Further, SLE impacts black women three times as often as Caucasian women. The condition is aggravated by sunlight. Symptoms include fever, weight loss, hair loss, mouth and nose sores, malaise, fatigue, seizures and symptoms of mental illness. Identification of a patient suffering SLE from is accomplished by identifying one or more of these symptoms in the patient. Ninety percent of patients experience joint inflammation similar to rheumatoid arthritis. Fifty percent develop a classic "butterfly" rash on the nose and cheeks. Raynaud's phenomenon (extreme sensitivity to cold in the hands and feet) appears in about 20 percent of people with SLE. Current treatments are limited to the use of anti-inflammatory drugs to control arthritis symptoms, and topical steroidal creams to treat skin lesions, while oral steroids, such as prednisone, are used for the systemic symptoms. One or more symptoms of SLE are reduced following treatment with *Bacillus coagulans* bacteria.

Rheumatoid Arthritis

Rheumatoid arthritis is a systemic disorder in which immune cells attack and inflame the membrane around joints. It also can affect the heart, lungs, and eyes. Of the estimated 2.1 million Americans with rheumatoid arthritis, approximately 1.5 million (71 percent) are women. Symptoms of the disease include inflamed and/or deformed joints, loss of strength, swelling, and pain. Identification of a patient suffering from rheumatoid arthritis is accomplished by identifying one or more of these symptoms in the patient. Current treatment modalities include rest and anti-inflammatory drugs. One or more symptoms of rheumatoid arthritis are reduced following treatment with *Bacillus coagulans* bacteria.

Scleroderma (Systemic Sclerosis)

Scleroderma involves the hyperactivity of certain immune cells, which produce fibrous, scar-like tissue in the skin, internal organs, and small blood vessels. It affects women three times more often than men overall, but increases to a rate 15 times greater for women during childbearing years, and appears to be more common among black women than Caucasian women. Symptoms of scleroderma include the appearance of Raynaud's phenomenon, as well as swelling and puffiness of the fingers or hands. Often, skin thickening follows, and other symptoms include skin ulcers on the fingers, joint stiffness in the hands, pain, sore throat, and diarrhea. Identification of a patient suffering from scleroderma is accomplished by identifying one or more of these symptoms in the patient. Current treatments of scleroderma include D-penicillamine, which has been shown to decrease skin thickening. This disorder also impacts other organs such as the kidneys, esophagus, intestines, and blood vessels and thus requires multi-system treatments. One or more symptoms of scleroderma are reduced following treatment with *Bacillus coagulans* bacteria.

Sjogren's Syndrome

Sjögren's syndrome (also called Sjögren's disease) is a chronic, slowly progressing inability to secrete saliva or tears. It can occur alone or with rheumatoid arthritis, scleroderma, or systemic lupus erythematosus. Nine out of 10 cases occur in women, most often at or around mid-life. Symptoms of this disorder include dryness of the eyes and mouth, swollen neck glands, difficulty swallowing or talking, unusual tastes or smells, thirst, tongue ulcers, or severe dental caries. Identification of a patient suffering from Sjögren's syndrome is accomplished by identifying one or more of these symptoms in the patient. Current treatments include interventions to keep the mouth and eyes moist (including drinking a lot of fluids and using eye drops, as well as good oral hygiene and eye care). One or more symptoms of Sjögren's syndrome are reduced following treatment with *Bacillus coagulans* bacteria.

Multiple Sclerosis (MS)

Multiple sclerosis is a disease of the central nervous system that usually first appears between the ages of 20 and 40; it affects women twice as often as men. MS is the leading cause of disability among young adults. MS is recognized to be an unpredictable disease of the central nervous system, and can range from relatively benign to somewhat disabling to devastating, as communication between the brain and other parts of the body is disrupted. Symptoms of MS include fatigue, problems walking, bowel and/or bladder disturbances, visual problems, changes in cognitive function, including problems with memory, attention, and problem-solving, abnormal sensations such as numbness or "pins and needles," changes in sexual function, pain, depression and/or mood swings, tremor, speech and swallowing problems, and impaired hearing. Identification of a patient suffering from multiple sclerosis is accomplished by identifying one or more of these symptoms in the patient. The vast majority of patients are mildly affected, but in the worst cases MS can render a person unable to write, speak, or walk. One or more symptoms of MS are reduced following treatment with *Bacillus coagulans* bacteria.

Myasthenia Gravis

Myasthenia gravis is a chronic autoimmune disorder characterized by gradual muscle weakness, often appearing first in the subject's face and often characterized by drooping eyelids, as well as double vision, difficulty breathing, talking, chewing, and swallowing. Identification of a patient suffering from myasthenia gravis is accomplished by identifying one or more of these symptoms in the patient. The drug edrophonium is currently used as a treatment, along with daily rest periods, which can improve muscle strength. One or more symptoms of myasthenia gravis are reduced following treatment with *Bacillus coagulans* bacteria.

Guillain-Barre Syndrome

Guillain-Barré syndrome is a disorder in which the body's immune system attacks part of the peripheral nervous system. The first symptoms of this disorder include varying degrees of weakness or tingling sensations in the legs. Identification of a patient suffering from Guillain-Barré syndrome is accomplished by identifying one or more of these symptoms in the patient. In many instances, the weakness and abnormal sensations spread to the arms and upper body. These symptoms can increase in intensity until the muscles cannot be used at all and the patient is almost totally paralyzed. In these cases, the disorder is life threatening and is considered a medical emergency. The patient is often put on a respirator to assist with breathing. Most patients, however, recover from even the most severe cases of Guillain-Barré syndrome, although some continue to have some degree of weakness. Guillain-Barré syndrome is rare. Usually Guillain-Barré occurs a few days or weeks after the patient has had symptoms of a respiratory or gastrointestinal viral infection. Occasionally, surgery or vaccinations will trigger the syndrome. The disorder can develop over the course of hours or days, or it may take up to 3 to 4 weeks. Because the signals traveling along the nerve are slower, a nerve conduction velocity (NCV) test is used to aid diagnosis. Increased protein in the cerebrospinal fluid is also used to diagnose Guillain-Barré syndrome. One or more symptoms of Guillain-Barré syndrome are reduced following treatment with *Bacillus coagulans* bacteria.

Hashimoto's Thryroiditis

Hashimoto's thyroiditis is a type of autoimmune disease in which the immune system destroys the thyroid, the gland that helps set the rate of metabolism. It attacks women 50 times more often than men. Symptoms of this disorder include low levels of thyroid hormone, resulting in mental and physical slowing, greater sensitivity to cold, weight gain, coarsening of the skin, and goiter (a swelling of the neck due to an enlarged thyroid gland). Identification of a patient suffering from Hashimoto's thyroiditis is accomplished by identifying one or more of these symptoms in the patient. Currently, thyroid hormone replacement therapy is used to treat this disorder. One or more symptoms of Hashimoto's thyroiditis are reduced following treatment with *Bacillus coagulans* bacteria.

Graves' Disease

Graves' disease is one of the most common autoimmune diseases, and impacts women about seven times as often as men. Subjects with Graves' disease produce an excessive amount of thyroid hormone. Symptoms of Graves' disease include weight loss due to increased energy expenditure, increased appetite, heart rate, and blood pressure, tremors, nervousness and sweating, as well as frequent bowel movements. Identification of a patient suffering from Graves' disease is accomplished by identifying one or more of these symptoms in the patient. Treatment options include anti-thyroid drug therapy or removal of the thyroid gland, e.g., surgically or by radioiodine treatment. One or more symptoms of Graves' disease are reduced following treatment with *Bacillus coagulans* bacteria.

Insulin-Dependent (Type 1) Diabetes

Type 1 diabetes is caused by too little insulin production in the pancreas, and usually occurs in children and young adults, but it can occur at any age. Symptoms include increased thirst, increased urination, weight loss, fatigue, nausea, vomiting, and frequent infections. Identification of a patient suffering from diabetes is accomplished by identifying one or more of these symptoms in the patient. Insulin treatment is the current treatment modality. One or more symptoms of diabetes are reduced following treatment with *Bacillus coagulans* bacteria.

Inflammatory Bowel Disease

Crohn's disease (also called ileitis or enteritis) causes inflammation in the small intestine. Crohn's disease usually occurs in the lower part of the small intestine, called the ileum, but it can affect any part of the digestive tract, from the mouth to the anus. The inflammation extends deep into the lining of the affected organ. The inflammation can cause pain and can make the intestines empty frequently, resulting in diarrhea. Identification of a patient suffering from Crohn's disease is accomplished by identifying one or more of these symptoms in the patient. Crohn's disease is one form of inflammatory bowel disease. Crohn's disease can be difficult to diagnose because its symptoms are similar to other intestinal disorders such as irritable bowel syndrome and to another type of IBD called ulcerative colitis. Ulcerative colitis causes inflammation and ulcers in the top layer of the lining of the large intestine. Crohn's disease affects men and women equally and seems to run in some families. About 20 percent of people with Crohn's disease have a blood relative with some form of IBD, most often a brother or sister and sometimes a parent or child. One or more symptoms of Crohn's disease are reduced following treatment with *Bacillus coagulans* bacteria.

Ulcerative Colitis

Ulcerative colitis is a disease that causes inflammation and sores, called ulcers, in the lining of the large intestine. The inflammation usually occurs in the rectum and lower part of the colon, but it may affect the entire colon. Ulcerative colitis rarely affects the small intestine except for the end section, called the terminal ileum. Ulcerative colitis may also be called colitis or proctitis. Symptoms of UC include fatigue, weight loss, loss of appetite, rectal bleeding and loss of body fluids and nutrients. Identification of a patient suffering from UC is accomplished by identifying one or more of these symptoms in the patient. The inflammation makes the colon empty frequently, causing diarrhea. Ulcers form in places where the inflammation has killed the cells lining the colon; the ulcers bleed and produce pus. Crohn's disease differs from ulcerative colitis because it causes inflammation deeper within the intestinal wall. Also, Crohn's disease usually occurs in the small intestine, although it can also occur in the mouth, esophagus, stomach, duodenum, large intestine, appendix, and anus. Ulcerative colitis may occur in people of any age, but most often it starts between ages 15 and 30, or less frequently between ages 50 and 70. Children and adolescents sometimes develop the disease. Ulcerative colitis affects men and women equally and appears to run in some families. One or more symptoms of UC are reduced following treatment with *Bacillus coagulans* bacteria.

Celiac Disease

Celiac disease is a digestive disease that damages the small intestine and interferes with absorption of nutrients from food. Subjects with celiac disease cannot tolerate a protein called gluten, which is found in wheat, rye, and barley. When people with celiac disease eat foods containing gluten, their immune system responds by damaging the small intestine. Specifically, the intestinal villi are lost, resulting in malnutrition. Symptoms of Celiac disease include diarrhea, abdominal pain and bloating, gas, irritability, depression, weight loss, delayed growth, failure to thrive in infants, anemia, and fatigue. Identification of a patient suffering from Celiac disease is accomplished by identifying one or more of these symptoms in the patient. Celiac disease is also known as celiac sprue, nontropical sprue, and gluten-sensitive enteropathy. Celiac disease may be induced following surgery, pregnancy, childbirth, viral infection, or severe emotional stress. One or more symptoms of Celiac disease are reduced following treatment with *Bacillus coagulans* bacteria.

Vasculitis Syndromes

This is a broad and heterogeneous group of diseases characterized by symptoms including inflammation and damage to the blood vessels, thought to be brought on by an autoimmune response. Identification of a patient suffering from vasculitis is accomplished by identifying one or more of these symptoms in the patient. Any type, size, and location of blood vessel may be involved. Vasculitis may occur alone or in combination with other diseases, and may be confined to one organ or involve several organ systems. One or more symptoms of vasculitis are reduced following treatment with *Bacillus coagulans* bacteria.

Hematologic Autoimmune Diseases

Blood also can be affected by an autoimmune disorder. In autoimmune hemolytic anemia, red blood cells are prematurely destroyed by antibodies. Other autoimmune diseases of the blood include autoimmune thrombocytopenic purpura and autoimmune neutropenia. One or more symptoms of these blood disorders are reduced following treatment with *Bacillus coagulans* bacteria.

The present inventors recognize that certain autoimmune disorders affect primarily women, as noted for several autoimmune disorders described above. The present invention discloses the prevention or treatment of an autoimmune disorder in a female subject. In embodiments of the invention, the autoimmune disorder to be treated or prevented in a female patient is Hashimoto's disease (also known as hypothyroiditis), systemic lupus erythematosus, Sjogren's syndrome, antiphospholipid syndrome, primary biliary cirrhosis, mixed connective tissue disease, chronic active hepatitis, Graves' disease (also termed hyperthyroiditis), rheumatoid arthritis, scleroderma, myasthenia gravis, multiple sclerosis, or chronic idiopathic thrombocytopenic purpura.

*Bacillus coagulans* Therapy Reduces Gastrointestinal Infection by Autoimmune Disease-Associated Pathogenic Microorganisms Many species of bacterial, mycotic and yeast pathogens possess the ability to cause a variety of disorders, including autoimmune disorders. *Bacillus coagulans*, a probiotic microorganism is useful in the prophylactic or therapeutic treatment of autoimmune conditions such as psoriasis, which are associated with infection by these aforementioned pathogens. Generally, *Bacillus coagulans* bacteria (i) possess the ability to produce and excrete enzymes useful in digestion (e.g., lactase, various proteases, lipases and amylases); (ii) demonstrate beneficial function within the gastrointestinal tract; (iii) serve to down-regulate the cytokine response as a result of bacterial/fungal/or mycotic interaction with the various mucosal cells; and (vi) are non-pathogenic. *Bacillus coagulans* bacteria are able to inhibit pathogenic yeast and other fungi, including *Candida albicans, Candida tropicalis* and *Trichophyton mentagrophytes, Trichophyton interdigitale, Trichophyton rubrum*, and *Trichophyton yaoundei*. *Bacillus coagulans* bacteria are also able to inhibit pathogenic bacteria, including *Staphylococcus* species, *Streptococcuspyogenes* species, *Pseudomonas* species, *Escherichia coli, Clostridium* species, *Gardnereia vaginailis, Proponbacterium acnes, Aeromonas* species, *Aspergillus* species; *Proteus* species; and *Klebsiella* species.

Strains of *Bacillus coagulans* bacteria are available from the American Type Culture Collection (ATCC), including the following accession numbers: *Bacillus coagulans* Hammer NRS 727 (ATCC No. 11014); *Bacillus coagulans* Hammer strain C (ATCC No. 11369); *Bacillus coagulans* Hammer (ATCC No. 31284); *Bacillus coagulans* Hammer NCA 4259 (ATCC No. 15949); and strains deposited under ATCC Accession Numbers 8038, 35670, 23498, 51232, 12245, 10545 and 7050. Purified *Bacillus coagulans* bacteria are also available from the Deutsche Sarumlung von Mikroorganismen und Zellkuturen GmbH (Braunschweig, Germany) using the following accession numbers: *Bacillus coagulans* Hammer 1915 (DSM No. 2356); *Bacillus coagulans* Hammer 1915 (DSM No. 2383, corresponds to ATCC No. 11014); *Bacillus coagulans* Hammer (DSM No. 2384, corresponds to ATCC No. 11369); and *Bacillus coagulans* Hammer (DSM No. 2385, corresponds to ATCC No. 15949). *Bacillus coagulans* bacteria can also be obtained from commercial suppliers such as K. K. Fermentation (Kyoto, Japan) and Nebraska Cultures (Walnut Creek, Calif.).

The *Bacillus coagulans* bacterial strain used to reduce infection by microbial pathogens is *Bacillus coagulans* hammer, or a strain derived therefrom. For example, the *Bacillus coagulans* bacterial strain is ATCC 31284, or a strain derived therefrom. These strains include, e.g., ATCC Numbers GBI-20, ATCC Designation Number PTA-6085, available to the public via the ATCC; GBI-30, ATCC Designation Number PTA-6086, available to the public via the ATCC; and GBI-40, ATCC Designation Number PTA-6087, available to the public via the ATCC; see U.S. Pat. No. 6,849,256 to Farmer, the contents of which are incorporated by reference in their entirety.

A composition comprising *Bacillus coagulans* bacteria in a pharmaceutically acceptable carrier suitable for oral administration to the gastrointestinal tract of a mammal (e.g., a human) animal is disclosed. *Bacillus coagulans* bacteria are provided in amounts sufficient to colonize the gastrointestinal tract of a mammal. The invention provides *Bacillus coagulans* bacteria at a concentration of from about $1 \times 10^4$ to about $1 \times 10^{12}$ viable bacteria, specifically about $1 \times 10^6$ to about $1 \times 10^{11}$, more specifically about $1 \times 10^8$ to about $1 \times 10^{10}$, and most specifically about $8 \times 10^8$. *Bacillus coagulans* bacteria are provided as vegetative cells, spores, or a combination thereof.

Vegetative cells are formulated in a composition that protects the cells from being killed by the acid environment of the stomach. Cells formulated in this manner successfully traverse the stomach to colonize the small and/or large intestine. Accordingly, the invention includes a composition containing a *Bacillus coagulans* bacterium in a pharmaceutically acceptable acid-resistant ("enteric") carrier. By acid-resistant is meant that the carrier or coating does not dissolve in an acidic environment. An acidic environment is characterized by a pH of less than 7. The acid-resistant carrier is resistant to acids at pH less than about 4.0. Preferably, the carrier does not dissolve in pH 2-3. Most preferably, it does not dissolve in pH of less than 2. To protect vegetative bacterial cells from stomach acids, the cells are coated or encapsulated with the acid-resistant carrier. The composition optionally includes other components such as glucose and phosphoric acid or other nutrient compounds to increase bacterial growth after removal of the carrier or coating. The invention also includes *Bacillus coagulans* bacteria in the form of spores, which are selected for the capability of germinating in the presence of bile acids such as cholic, deoxycholic and tauro-deoxycholic acids. Enterically coated and bile acid-resistant *Bacillus coagulans* bacteria are described in U.S. Ser. No. 10/287,904, filed Nov. 5, 2002, the contents of which are incorporated by reference in their entirety.

The compositions contain *Bacillus coagulans* bacteria and one or more biologically active compounds; such as a natural or synthetic compound that decreases or relieves a symptom of psoriasis. Exemplary compounds include immunosuppressants including methotrexate, cyclosporine, hydroxyurea, mycophenolate mofetil, sulfasalazine, 6-thioguanine, and other compounds such as retinoids.

Example 1

Preparation of *Bacillus coagulans* Bacteria

I. Preparation of Vegetative *Bacillus coagulans*

*Bacillus coagulans* is aerobic and facultative, and is typically cultured at pH 5.7 to 6.8, in a nutrient broth containing up to 2% (by wt) NaCl, although neither NaCl, nor KCl are required for growth. A pH of about 4.0 to about 7.5 is optimum for initiation of sporulation (i.e., the formation of spores). The bacteria are optimally grown at 20° C. to 45° C., and the spores can withstand pasteurization. Additionally, the bacteria exhibit facultative and heterotrophic growth by utilizing a nitrate or sulfate source. *Bacillus coagulans* strains and their growth requirements have been described previously (see e.g., Baker, D. et al, 1960. *Can. J Microbiol.* 6: 557-563; Nakamura, H. et al, 1988. *Int. J. Syst. Bacteriol.* 38: 63-73. In addition, various strains of *Bacillus coagulans* can also be isolated from natural sources (e.g., heat-treated soil samples) using well-known procedures (see e.g., *Bergey's Manual of Systemic Bacteriology*, Vol. 2, p. 1117, Sneath, P. H. A. et al., eds. Williams & Wilkins, Baltimore, Md., 1986).

*Bacillus coagulans* bacteria are cultured in a variety of media, although it has been demonstrated that certain growth conditions are more efficacious at producing a culture that yields a high level of sporulation. For example, sporulation enhanced by supplementing the culture medium with 10 mg/l of $MgSO_4$ sulfate, yielding a ratio of spores to vegetative cells of approximately 80:20. In addition, certain culture conditions produce a bacterial spore that contains a spectrum of metabolic enzymes particularly suited for the present invention (i.e., production of lactic acid and enzymes for the enhanced probiotic activity and biodegradation). Although the spores produced by these aforementioned culture conditions are preferred, various other compatible culture conditions that produce viable *Bacillus coagulans* spores are utilized in the practice of the present invention.

Suitable media for the culture of *Bacillus coagulans* include: TSB (Tryptic Soy Broth), GYE (Glucose Yeast Extract Broth), and NB (nutrient broth), which are all well known within the field and available from a variety of sources. Media supplements which contain enzymatic digests of poultry and/or fish tissue, and containing food yeast are particularly preferred. A preferred supplement produces a media containing at least 60% protein, and about 20% complex carbohydrates and 6% lipids. Media can be obtained from a variety of commercial sources, notably DIFCO (Newark, N.J.); BBL (Cockeyesville, Md.); and Troy Biologicals (Troy, Md.)

II. Preparation of *Bacillus coagulans* Spores

A culture of dried *Bacillus coagulans* Hammer bacteria (ATCC No. 31284) spores was prepared as follows. Approximately $1 \times 10^7$ spores were inoculated into one liter of culture medium containing: 30 g (wt./vol.) Tryptic Soy Broth; 10 g of an enzymatic-digest of poultry and fish tissue; and 10 g $MnSO_4$. The culture was maintained for 72 hours under a high oxygen environment at 37° C. so as to produce a culture having approximately $6 \times 10^9$ cells/gram of culture. The culture was then centrifuged to remove the liquid culture medium and the resulting bacterial paste was re-suspended in 100 ml of sterile water and 20% malto-dextrin and lyophilized. The lyophilized bacteria were ground to a fine powder by use of standard good manufacturing practice (GMP) methodologies.

Example 2

Formulations and Administration

Vegetative bacterial cells and spores are administered at a dose of $10,000-10^{11}$ cells per administration. A typical therapeutic composition of the present invention contains in a one-gram dosage formulation, from approximately $1 \times 10^3$ to $1 \times 10^{12}$, and preferably approximately $2 \times 10^5$ to $2 \times 10^{10}$, colony-forming units (CFU) of viable *Bacillus* bacteria (i.e., vegetative bacteria) or bacterial spores. Typically, *Bacillus coagulans* bacteria remain in and colonize the colon for a period of 3-5 days post-administration.

| Formulation #1 | |
|---|---|
| *Bacillus coagulans* | $8.0 \times 10^8$ (53 mg) |
| *Saccharomyces boulardii* | $1.5 \times 10^8$ (7.5 mg) |
| Copper Sulfate | 5 mcg |
| Vitamin C | 50 mg |
| Selenium | 2.5 mcg |
| Micro-Crystalline Cellulose | 132 mg |
| Total 250 mg | |
| Formulation #2 | |
| *Bacillus coagulans* | $8.0 \times 10^8$ (53 mg) |
| *Saccharomyces boulardii* | $1.5 \times 10^8$ (7.5 mg) |
| L-Lysine | 75 mg |
| Maltodextrin | 35 mg |
| Blue lake #1 Dye | 1 mg |
| Aspartame | 2 mg |
| Compressible Sugars | 173 mg |
| Total 350 mg | |
| Formulation #3 | |
| *Bacillus coagulans* | $1.5 \times 10^9$ (100 mg) |
| Maltodextrin | 35 mg |
| Microcrystalline Cellulose | 140 mg |
| Total 350 mg | |
| Formulation #4 | |
| *Bacillus coagulans* | $1.5 \times 10^9$ (100 mg) |
| *Sarccharomyces boulardii* | $2.5 \times 10^8$ (12.5 mg) |
| L-Lysine | 75 mg |
| Microcrystalline Cellulose | 163 mg |

-continued

| Total 350 mg | |
|---|---|
| Formulation #5 | |
| Bacillus coagulans | $1.5 \times 10^9$ (100 mg) |
| L-Lysine | 75 mg |
| Fluconazole 2% | 150 mg |
| Filler | 25 mg |
| Total 350 mg | |

The invention provides for the addition of other useful ingredients. Many individuals that suffer from immune disorders of this nature also have been shown to have vitamin and mineral deficiencies. Hence, addition of vitamin and mineral supplements is useful for the dietary management of these disorders.

Example 3

Use of *Bacillus coagulans* Bacteria in the Treatment and Clinical Remission of Chronic Psoriasis Probiotic bacteria reduce the numbers of pathogens in the gut of humans and animals. In addition, *Bacillus coagulans* bacteria downregulate the body's cytokine response to toxins and pathogenic organisms.

A number of deleterious microorganisms promote overstimulation of immune system. In the case of psoriasis, this leads to the production of cytokines (TNF-a) that cause the formation of dermal plates. *Candida albicans* is the underlying infection in these circumstances. It is common for physicians today to prescribe systemic antifungal compounds to reduce psoriatic lesions. Unfortunately, the antifungal most often used in these circumstances is Fluconazole, which can only be used for 30 days (as per FDA guidelines). With these issues in mind, studies were carried out to determine whether *Bacillus coagulans* lactic acid bacteria could be employed to reduce the number of *Candida* species in the stool while down regulating the production of TNF-a as a result of the *Candida* infection.

Twelve human patients with chronic psoriasis were studied at a General practice clinic in Cleveland, Ohio over a three-month period. Patients were provided with capsules containing *Bacillus coagulans* bacteria ($7.5 \times 10^8$ colony forming units (CFU)) and microcrystalline cellulose as a carrier, and instructed to take two capsules per day. There were no restrictions on the time of day of consumption or if the two capsules were taken at the same or different times during the day. The treatment lasted three months; patients were observed at the beginning and end of the treatment.

Results after a two-month period indicated that *Bacillus coagulans* therapy was nearly 100% effective in reducing the surface area of psoriatic plates in patients suffering from Psoriasis vulgaris. The physician that conducted the study did not that a few younger patients (16-25 years of age) that had plates over >60% of their respective bodies did show results much quicker than the patients that were older (50 years of age or older), and had been affected by the disease for a much longer period (>20 years). Five patients that showed excellent results after therapy discontinued use of the formulation (for various reasons) and their psoriatic plates returned very quickly. After re-initiating therapy, the plates started to recede again. This indicates that the underlying *Candida* infection may not be totally eliminated and that a longer period of therapy may be required to maintain the results. Moreover, some individuals are more susceptible to mycotic infection and as a result, these individuals need to manage this state with continued use of the formulation. The usage parameters may be different for dietary management after initial results but, to guarantee that the initial results are maintained, the a minimum of one capsule a day ongoing may be sufficient.

Example 4

Use of *Bacillus coagulans* Bacteria to Reduce Serum TNF-α Levels

Colonization of the mammalian gastrointestinal tract by pathogenic microorganisms leads to the aberrant production of cytokines (e.g., TNF-α), which cause symptoms of psoriasis, such as dermal plates. Oral administration of *Bacillus coagulans* bacteria is examined for the ability to decrease cytokine production in human subjects suffering from or at risk of developing psoriasis.

Materials and Methods

Subjects are identified by the presence or past incidence of one or more symptoms of psoriasis, or by a family history of the disease (one or more parents, grandparents or siblings having one or more symptoms of psoriasis). Non-affected individuals are used as controls. Serum cytokine levels are determined prior to *Bacillus coagulans* bacteria treatment, at regular intervals throughout the duration of the treatment, and upon completion of the treatment. Measured cytokines include TNF-α and interleukin-6 (IL-6). Measurement of serum cytokine levels is performed by methods known in the art, such as ELISA. *Bacillus coagulans* bacteria are administered to affected and non-affected subjects such that at least about $1 \times 10^6$ viable *Bacillus coagulans* bacteria are delivered in the gastrointestinal tract of each subject per day. Treatments last at least about 10 days, e.g., about 10, 15, 20, 30, 45, 60, 75, 90 or 120 days.

Results

Human patients suffering from or at risk of developing psoriasis have higher levels of TNF-α than non-affected controls. Treatment with *Bacillus coagulans* bacteria results in a decrease in serum TNF-α levels in affected subjects.

Example 5

Medical Foods Containing *Bacillus coagulans* Bacteria

A "medical food" means a food which is formulated to be consumed or administered enterically under the supervision of a physician and which is intended for the specific dietary management of a disease or condition for which distinctive nutritional requirements, based on recognized scientific principles, are established by medical evaluation. (See, 21 USC 360ee(b)(3)). For subjects suffering from or at risk of developing an autoimmune disease, the compositions containing *Bacillus coagulans* bacteria are nutritionally complete formulas of medical foods. Alternatively, the compositions containing *Bacillus coagulans* bacteria are nutritionally incomplete formulas of medical foods.

Medical foods containing *Bacillus coagulans* bacteria are specially formulated and processed for subjects suffering from or at risk of developing an autoimmune disease, such as a subject who requires the medical as a major treatment modality. Typically, the medical foods containing *Bacillus coagulans* bacteria medical foods are formulated as an enteral nutrition product, i.e., it is provided through the gastrointestinal tract, taken by mouth, or provided through a tube or catheter that delivers nutrients beyond the oral cavity or directly to the stomach. The medical food is formulated to provide at least about $1 \times 10^6$ viable *Bacillus coagulans* bacteria in the gastrointestinal tract of a mammalian subject per day, based on a serving size of about 1 gram to about 2 grams of the medical food taken up to about twice a day. The medical food also optionally includes a non-microbially derived anti-fungal agent, an immunosuppressive agent, or a non-microbially derived anti-fungal agent and an immunosuppressive agent.

Subjects for whom medical foods containing *Bacillus coagulans* bacteria are appropriate are identified by the presence or past incidence of one or more symptoms of an autoimmune disease such as psoriasis, or by a family history of the disease (one or more parents, grandparents or siblings having one or more symptoms of an autoimmune disease).

Example 6

Use of *Bacillus coagulans* Bacteria in the Treatment of Other Autoimmune Disorders Twelve human patients with Crohn's disease were studied at a general practice clinic in Cleveland, Ohio over a one-month period. Patients were provided with capsules containing *Bacillus coagulans* bacteria ($1.5 \times 10^9$ colony forming units (CFU)) and microcrystalline cellulose as a carrier, and instructed to take one capsule per day. There were no restrictions on the time of day of consumption. The treatment lasted one month; patients were observed at the beginning and end of the treatment.

Results after one month indicated that all 11 out of 12 patients responded well to the formulation. One patient dropped out without explanation. The incidence of diarrhea was reduced by over 75% and abdominal pain and spasms were reduced significantly. Crohn's disease is diagnosed symptomatically; thus, a significant reduction in the number and severity of symptoms experienced each day is a notable improvement in individuals that suffer from this disease.

Other embodiments are within the following claims.

What is claimed is:

1. A method of reducing a symptom of psoriasis, comprising identifying a patient suffering from or at risk of developing psoriasis, and orally administering to said patient a composition comprising *Bacillus coagulans* bacteria in an amount effective to reduce serum TNF-α levels in said patient, wherein said bacteria is selected from the group consisting of GBI-20 (ATCC Designation Number PTA-6085), GBI-30 (ATCC Designation Number PTA-6086), and GBI-40 (ATCC Designation Number PTA-6087).

2. The method of claim 1, wherein said composition further comprises an antifungal agent.

3. The method of claim 2, wherein said antifungal agent is selected from the group consisting of clotrimazole, fluconazole, itraconazole, ketoconazole, miconazole, nystatin, terbinafine, terconazole, and tioconazole.

4. The method of claim 1, wherein said symptom is selected from the group consisting of scaling, blistering, skin lesions, itchiness, and joint pain.

5. The method of claim 1, wherein said composition further comprises an immunosuppressive agent.

6. The method of claim 5, wherein said immunosuppressive agent is selected from the group consisting of methotrexate, cyclosporine, hydroxyurea, mycophenolate mofetil, sulfasalazine, and 6-thioguanine.

7. The method of claim 1, wherein said composition further comprises a retinoid.

8. The method of claim 1, wherein said *Bacillus coagulans* bacteria are provided at a concentration of from about $1 \times 10^8$ to about $1 \times 10^{10}$ colony forming units of viable bacteria.

9. The method of claim 1, wherein said *Bacillus coagulans* bacteria are provided at a concentration of from about $1 \times 10^9$ to about $2 \times 10^9$ colony forming units of viable bacteria.

10. The method of claim 1, wherein the *Bacillus coagulans* bacteria are in the form of spores.

11. The method of claim 1, wherein the *Bacillus coagulans* bacteria are in the form of vegetative cells.

12. The method of claim 1, wherein said composition further comprises an antibiotic agent, wherein said antibiotic agent is selected from the group consisting of gentamicin, vancomycin, oxacillin, tetracycline, nitroflurantoin, chloramphenicol, clindamycin, trimethoprim sulfamethoxasole, cefaclor, cefadroxil, cefixime, cefprozil, ceftriaxone, cefuroxime, cephalexin, loracarbef, ampicillin, amoxicillin clavulanate, bacampicillin, cloxicillin, penicillin VK, ciprofloxacin, grepafloxacin, levofloxacin, lomefloxacin, norfloxacin, ofloxacin, sparfloxacin, trovafloxacin, azithromycin, and rythromycin.

13. The method of claim 12, wherein said composition further comprises an anti-fungal agent.

14. The method of claim 1, wherein said composition is orally administered about once every day for about 3 days.

15. The method of claim 1, wherein said composition is orally administered about once every day for about 7 days.

16. The method of claim 1, wherein said composition further comprises a vitamin, a mineral, or an antioxidant.

17. The method of claim 1, wherein said bacteria is GBI-20 (ATCC Designation Number PTA-6085).

18. The method of claim 1, wherein said bacteria is GBI-30 (ATCC Designation Number PTA-6086).

19. The method of claim 1, wherein said bacteria is GBI-40 (ATCC Designation Number PTA-6087).

20. A method of reducing a symptom of Crohn's Disease, comprising identifying a patient suffering from or at risk of developing Crohn's Disease, and orally administering to said patient a composition comprising *Bacillus coagulans* bacteria in an amount effective to reduce serum TNF-α levels in said patient, wherein said bacteria is selected from the group consisting of GBI-20 (ATCC Designation Number PTA-6085), GBI-30 (ATCC Designation Number PTA-6086), and GBI-40 (ATCC Designation Number PTA-6087).

21. The method of claim 20, wherein said symptom is selected from the group consisting of diarrhea, abdominal pain, rectal bleeding, fever, nausea, weight loss, lethargy and loss of appetite.

22. The method of claim 20, wherein said composition is orally administered about once every day for about 3 days.

23. The method of claim 20, wherein said composition is orally administered about once every day for about 7 days.

24. The method of claim 20, wherein said composition further comprises a vitamin, a mineral, or an antioxidant.

25. The method of claim 20, wherein said bacteria is GBI-20 (ATCC Designation Number PTA-6085).

26. The method of claim 20, wherein said bacteria is GBI-30 (ATCC Designation Number PTA-6086).

27. The method of claim 20, wherein said bacteria is GBI-40 (ATCC Designation Number PTA-6087).

* * * * *